United States Patent [19]

Robinson et al.

[11] Patent Number: 5,211,748
[45] Date of Patent: May 18, 1993

[54] IDENTIFIABLE DENTAL RESTORATIVE MATERIAL

[75] Inventors: Peter B. Robinson, London; Brian J. Millar, Beckenham, both of England

[73] Assignee: National Research Development Corporation, London, England

[21] Appl. No.: 819,638

[22] Filed: Jan. 10, 1992

Related U.S. Application Data

[63] Continuation of Ser. No. 489,943, Mar. 9, 1990, abandoned.

[30] Foreign Application Priority Data

Mar. 21, 1989 [GB] United Kingdom ............... 8906484

[51] Int. Cl.$^5$ ................................................ C09K 3/00
[52] U.S. Cl. .................................. 106/35; 433/228.1; 501/132
[58] Field of Search ............... 106/35; 433/228.1; 501/132

[56] References Cited

U.S. PATENT DOCUMENTS

| | | | |
|---|---|---|---|
| 4,167,417 | 9/1979 | Franz et al. | 106/35 |
| 4,150,012 | 10/1979 | Joos | 260/42.15 |
| 4,170,823 | 4/1979 | Smyth et al. | 32/8 |
| 4,198,244 | 4/1980 | Binns et al. | 106/35 |
| 4,491,453 | 1/1985 | Koblitz et al. | 433/217 |
| 4,514,174 | 4/1985 | Dougherty et al. | 433/226 |
| 4,600,389 | 7/1986 | Schwartz | 433/217.1 |
| 4,746,685 | 5/1988 | Masuhara et al. | 522/13 |
| 4,957,441 | 9/1990 | Bryan | 433/288.1 |
| 5,012,461 | 4/1992 | Rheinberger et al. | 106/35 |
| 5,015,180 | 5/1991 | Randklev | 433/9 |
| 5,035,621 | 7/1991 | Gottschalk et al. | 433/226 |

FOREIGN PATENT DOCUMENTS

| | | |
|---|---|---|
| 1107892 | 5/1961 | Fed. Rep. of Germany . |
| 1963552 | 8/1970 | Fed. Rep. of Germany . |
| 1471000 | 1/1967 | France . |
| 2064550A | 6/1981 | United Kingdom . |

*Primary Examiner*—Mark L. Bell
*Assistant Examiner*—Alan Wright
*Attorney, Agent, or Firm*—Nixon & Vanderhye

[57] ABSTRACT

A problem on removing dental restorative material can be to know its exact extent, otherwise sound tooth material may be unnecessarily removed. The inventive restorative material is made identifiable by adding crushed ruby powder, which fluoresces under standard dental blue light.

17 Claims, No Drawings

IDENTIFIABLE DENTAL RESTORATIVE MATERIAL

This is a continuation of application Ser. No. 07/489,943, filed Mar. 9, 1990, now abandoned.

This invention relates to a dental restorative material which can be identified as such when the need arises.

All dental restorative materials may at some stage need to be removed for various reasons including recurrent caries, staining or concern over general integrity. It is known that, when removing an amalgam restoration, the dentist will tend to increase the size of the cavity in the tooth, in other words unnecessarily removing perfectly sound tooth material. This may weaken the remaining tooth.

Amalgam is being increasingly replaced by composite resin restorations and glass ionomer cements, and these materials will doubly exacerbate the problem. The latter materials are chemically bonded to the dentine and enamel of the tooth (unlike amalgam, the last fragments of which are easy to remove); composite resins in particular, and increasingly newer glass ionomer restorations, are carefully formulated to colour-match natural teeth (unlike amalgam, which is grey, making it plain whether it has all been removed).

The inventors have conducted a pilot study revealing a large variation between the dimensions of the original tooth cavity and that following the removal of bonded, tooth coloured filling materials. Two-thirds of cavities increased in size (overcutting) by up to 130% (mean 36%), while the remaining one-third of cavities decreased in size by up to 35% (mean 21%) because of retained undetected composite material. This indicates the difficulty of removing composite resin restorations from cavities, one reason being their tooth-like appearance. Another reason is the not dissimilar 'feel' of tooth and composite resin. A way of differentiating between tooth and composite is therefore needed.

While it might be possible to devise a dye which would differentially stain tooth and composite, this has not so far been satisfactorily achieved. (Composite resin has been successful because it is designed not to stain.) Composite resins containing an ultra-violet fluorescing additive have been used in the past, but only for sealing fissures, and to make it easier to confirm later that they had been retained in position. They have been discontinued because ultra-violet light is hazardous to the eyesight of the dental personnel and patients. Acid-etching the adjacent enamel would assist differentiation, but it is time-consuming and undesirable.

According to the present invention, therefore, a dental restorative material is characterised by an additive which luminesces when irradiated by visible-wavelength light. The irradiating wavelength should preferably be that emitted by already available composite-curing light sources used in dental practice, viz. a blue light, and preferably the additive does not fluoresce when irradiated by ultraviolet light. The additive should be biocompatible (non-toxic, non-irritating, non-radioactive), chemically compatible with the restorative material and non-weakening to the restorative material. The additive may replace some of the filler in composite resins or glass in glass ionomer cements. A suitable additive is chromium-activated ruby, a mixed aluminium/chromium oxide. Ruby can play both a cosmetic (luminescing) and a structural role in a generally aluminosilicate structure as found in glass ionomer cements.

The invention will now be described by way of example.

A composite resin suited for use in posterior teeth, containing 80% filler (barium-glass or quartz particles of size <15 μm) and 20% urethane dimethacrylate, was mixed with 10% by volume of crystalline ruby crushed to a particle size of about 100 μm. Ruby is corundum $Al_2O_3$ with some $Cr_2O_3$.

This resin with crushed-ruby additive was used as a dental restorative material in a cavity in a recently extracted human tooth. The resin was placed incrementally and cured in the normal way using blue light. For inspection during this work, the same blue light was directed from a standard dental source (for light-curing resins) onto the resin, which fluoresced, and glowed pink. This 2-3 second exposure showed where the resin was, without prematurely curing it (for which some 40 seconds' exposure is needed). This assisted with the avoidance of air pockets and the accurate placement and finishing of the restorative material (in particular, without flash over the cavity margin) before final light-curing. The aesthetic quality (colour, translucency) was not adversely affected by the ruby additive.

The task was then undertaken of removing the restoration from the tooth. Blue light was directed from a standard dental source (for light-curing resins) onto the resin, which fluoresced, and glowed pink. Because the restorative material showed up so clearly, it could be entirely removed with greater accuracy and so reduce the loss of natural tooth. Where clinically expedient, part of the restorative could be left in place.

Blue light is used in the invention because it is readily available as standard dental equipment in the surgery. Ultra-violet light is not used in the example, to save damage to the eyesight of dental personnel and patients, and conveniently the additive (ruby) scarcely luminesces in ultra-violet anyway, which saves the patient from being discountenanced in trendy discotheques. Natural teeth also scarcely luminesce in ultra-violet.

Lining cements are included in the definition of restorative materials. As the base of a cavity is not necessarily lined, a lining cement according to the invention would not by itself be sufficient to aid accurate removal, but it would be better than nothing as it would at least help to identify the border of the cavity at the tooth surface. In certain circumstances they could be useful in their own right.

When crowning a tooth, the dentist may first place a "core" to support the crown. If the core is luminescent according to the invention, this is of great assistance in cutting the core to a shape suitable for receiving a crown, because the composite is distinguishable from tooth.

Materials according to the invention can also be used as identifiable fissure sealants and luting composites, whose identifiability would be useful during cementation of composite-cement-retained inlays, onlays, crowns, bridges and veneers.

Identifiable cement materials according to the invention may simplify cement removal following the detachment of composite-cement-retained orthodontic and splinting appliances.

We claim:

1. A dental restorative composition comprising a dental restorative material and an additive which luminesces when irradiated by visible-wavelength light and does not luminesce when irradiated by ultraviolet light.

2. A composition according to claim 1, wherein said additive luminesces when irradiated by blue light.

3. A composition according to claim 1, which is a composite resin, wherein said additive acts as a filler.

4. A composition according to claim 1, which is a glass ionomer cement, wherein said additive acts as a glass of the glass ionomer.

5. A composition according to claim 1, wherein said additive is chromium-activated ruby.

6. A composition according to claim 1, wherein said dental restorative material comprises about 80% by weight of a filler and about 20% by weight urethane dimethacrylate, and said additive is crushed crystalline ruby.

7. A composition according to claim 6, wherein said dental restorative material comprises about 10% by volume of said crushed crystalline ruby.

8. A method of differentiating tooth material from a dental restorative composition comprising a dental restorative material and an additive which luminesces when irradiated by visible-wavelength light and does not luminesce when irradiated by ultraviolet light, said method comprising the step of:

irradiating the tooth to cause the dental restorative composition to luminesce.

9. A method according to claim 8, wherein said additive luminesces when irradiated by blue light.

10. A method according to claim 8, wherein said dental restorative composition is a composite resin in which the additive acts as a filler.

11. A method according to claim 8, wherein said dental restorative composition is a glass ionomer cement and the additive acts as a glass of the glass ionomer.

12. A method according to claim 8, wherein the additive is chromium-activated ruby.

13. A method for restoring a tooth, comprising the steps of:

introducing a dental restorative composition into the tooth to be restored, said dental restorative composition comprising a dental restorative material and an additive which luminesces when irradiated by visible-wavelength light and which does not luminesce when irradiated by ultraviolet light; and inspecting the introduced dental restorative composition by irradiating said dental restorative composition to determine the location of said restorative composition in the tooth and thereby ensure accurate restoration of the tooth.

14. A method according to claim 13, wherein said additive luminesces when irradiated by blue light.

15. A method according to claim 13, wherein said dental restorative composition is a composite resin and said additive acts as a filler.

16. A method according to claim 13, wherein said dental restorative composition is a glass ionomer cement and said additive acts as a glass of the glass ionomer.

17. A method according to claim 13, wherein said additive is chromium-activated ruby.

* * * * *